United States Patent [19]

Ling et al.

[11] Patent Number: 5,223,400

[45] Date of Patent: Jun. 29, 1993

[54] IMMUNOASSAY METHOD FOR DETERMINING THE SPECIFICITY OF BINDING OF A MONOCLONAL ANTIBODY TO AN ANTIGEN

[75] Inventors: Victor Ling; Elias Georges, both of Toronto, Canada

[73] Assignee: The Ontario Cancer Institute, Toronto, Canada

[21] Appl. No.: 360,199

[22] Filed: Jun. 1, 1989

[51] Int. Cl.⁵ .......................... C12Q 1/00; C12Q 1/70
[52] U.S. Cl. .................................. 435/7.93; 435/7.1; 435/5
[58] Field of Search .................. 435/7, 5, 6, 7.93, 7.1

[56] References Cited

PUBLICATIONS

Geysen et al. *PNAS* 81:3998–4002 (1984).
Riordan et al. *Nature* 316, 817–819 (1985).
Endicott et al. *Mol. Cell Biol.* 7, 4075–4081 (1987).

*Primary Examiner*—Margaret Moskowitz
*Assistant Examiner*—Bradley L. Sisson
*Attorney, Agent, or Firm*—Ridout & Maybee

[57] ABSTRACT

An immunoassay method for determining the specificity of binding of a monoclonal antibody to an antigen is afforded by comparing the binding of antibody and antigen both with and without the addition of excess epitope specific peptide.

8 Claims, 7 Drawing Sheets

| C-Terminal Domain | C219 mAb | C494 mAb | C32 mAb |
|---|---|---|---|
| Class I | | | |
| Hamster (pgp1) | VVQEALD | PNTLEGN | GDNSRVVSQDEIERAA |
| Human (mdr1) | VVQEALD | PNTLEGN | GDNSRVVSQEEIVRAA |
| Class II | | | |
| Hamster (pgp2) | VVQEALD | PNWLEGN | GDNSRVVSQDEIERAA |
| Mouse (mdr1) | VVQEALD | PTLLEGN | GDNSRAVSHEEIVRAA |
| Class III | | | |
| Hamster (pgp3) | VVQEALD | -DKFEGS | GDNSRVVSQDEIVRAA |
| Human (mdr3) | VVQEALD | PDKFEGN | GDNSRVVSQDEIVRAA |
| Mouse (mdr2) | VVQEALD | PDKFEGN | GDNSRVVPHDEIVRAA |
| N-Terminal Domain | | | |
| Hamster (pgp2) | VVQAALD | GNLEFRN | |
| Human (mdr1) | VVQVALD | GNLEFKN | |
| Mouse (mdr1) | VVQAALD | GNLEFSD | |
| Mouse (mdr2) | EVQAALD | | |

FIG 3

C219 mAb Binding Sequence

| C-Terminal Domain | | Peptide | Signal |
|---|---|---|---|
| Classes I, II, III | | VVQEALD | ++ |

| N-Terminal Domain | | | |
|---|---|---|---|
| Classes I, II, III | | VVQAALD | ++++ |
| Class I | (Human ;mdr1) | VVQVALD | + |

C494 mAb Binding Sequence

| C-Terminal Domain | | Peptide | Signal |
|---|---|---|---|
| Class I | (Hamster;pgp1) | PNTLEGN | ++++ |
|  | (Human ;mdr1) | PNTLEGN | ++++ |
| Class II | (Hamster;pgp2) | PNWLEGN | − |
|  | (Mouse ;mdr1) | PTLLEGN | − |
| Class III | (Hamster;pgp3) | PDKFEGS | − |
|  | (Human ;mdr3) | PDKFEGN | − |

C32 mAb Binding Sequence

| C-Terminal Domain | | Peptide | Signal |
|---|---|---|---|
| Class I | (Hamster;pgp1) | SQDEIER | ++++ |
|  | (Human ;mdr1) | SQEEIVR | − |
| Class II | (Hamster;pgp2) | SQDEIER | ++++ |
|  | (Mouse ;mdr1) | SHEEIVR | − |
| Class III | (Hamster;pgp3) | SQDEIVS | − |
|  | (Mouse ;mdr2) | PHDEIVR | − |

FIG. 4

IMMUNOASSAY METHOD FOR DETERMINING THE SPECIFICITY OF BINDING OF A MONOCLONAL ANTIBODY TO AN ANTIGEN

The invention is an immunoassay method for determining the specificity of binding of a monoclonal antibody to an antigen, and thereby enhancing the sensitivity of the assay. The invention makes use of epitope characterization to provide peptides encoding epitopes. Comparative binding studies of antibody to antigenic substances with or without the addition of the epitopic peptide enables the determination of the specificity of antibody binding.

Immunoassays are routinely used in a wide variety of diagnostic and analytical applications. With the relatively recent availability of monoclonal antibodies, the power of immunoassays to focus on a particular antigen target is greatly increased. However, when antibody binding is observed in one of these assays, it is possible that such binding may be nonspecific, that is, does not result from epitope specific antibody-antigen binding; and therefore, gives a false positive result. Accordingly, it is desirable to be able to augment the power of a monoclonal antibody immunoassay with the determination that the observed binding is epitope specific. Such a determination also serves to enhance the sensitivity of the assay.

The invention addresses this need and is applicable to virtually any immunoassay method as, for example, ELISA, RIA or immunohistochemical staining. The present method enhances the power of immunoassays employing monoclonal antibodies for which epitope encoding peptides are known by enabling the user of the assay to ensure the specificity of binding being observed.

Accordingly, the present invention provides an immunoassay method for determining the specificity of binding of a monoclonal antibody to an antigen, comprising the steps of:

a) contacting a first portion of a test substance with the monoclonal antibody, incubating the resulting mixture to promote binding of the antibody to available antigen associated with the test substance, and testing for binding of antibody to the test substance;

b) if binding of antibody to the first portion of test substance is demonstrated, contacting a second portion of the test substance with the monoclonal antibody which has been pre-incubated with at least an excess amount of a peptide encoding the antibody epitope for the antigen sufficient to ensure occupation of substantially all antibody binding sites for the epitope, incubating the resulting mixture to promote binding of the antibody to any available antigen associated with the test substance, and testing for binding of antibody to the test substance; and c) comparing the results for the binding of the antibody to the first and second portions of the test substance to determine the specificity of antibody binding.

The invention will be described in relation to a particular antibody/antigen system, but it should be understood that the following description is not intended to limit the scope of the general method of the invention which has broad application.

BRIEF DESCRIPTION OF THE DRAWINGS

FIG. 3 shows a comparison of the potential C219, C494, and C32 binding sequences among P-glycoprotein gene family in hamster, human, and mouse. The P-glycoprotein tandem repeats (as illustrated in FIG. 2) are referred to as C- and N-terminal domains. The potential antibody binding sequences from the different gene members in hamster, human, and mouse have been classified based on the hamster numbering system. The notation in the closed brackets correspond to the designation given to each gene member. Bold letter amino acids for each epitope indicate the position of the critical residues for antibody binding.

FIG. 4 shows a comparison of antibody binding to peptide analogues of their binding sequences. The different peptide analogues for C219, C494, and C32 have been tested for their binding to their respective antibodies. The values of the substrate absorbance at 405-630 nm have been converted to plus signs as in FIG. 2. The species origin and the gene member of the P-glycoprotein gene family as found in the literature are indicated in the closed brackets. The bold letter amino acids represent some of the different amino acids between the analogue and the antibody binding sequence.

FIG. 5a shows ascending colon stained with C494 mAb, and FIG. 5b shows the same system in the presence of the peptide KPNTLEGNVKC. FIG. 5c shows adrenal gland stained with C32 mAb, and FIG. 5d shows the same system in the presence of the peptide GDNSRVVSQDEIERAAC. FIG. 5e shows skeletal muscle from the chest wall stained with C219 mAb, and FIG. 5f shows the same system in the presence of the peptide VVQEALDKAREGRTC.

Figure 1:
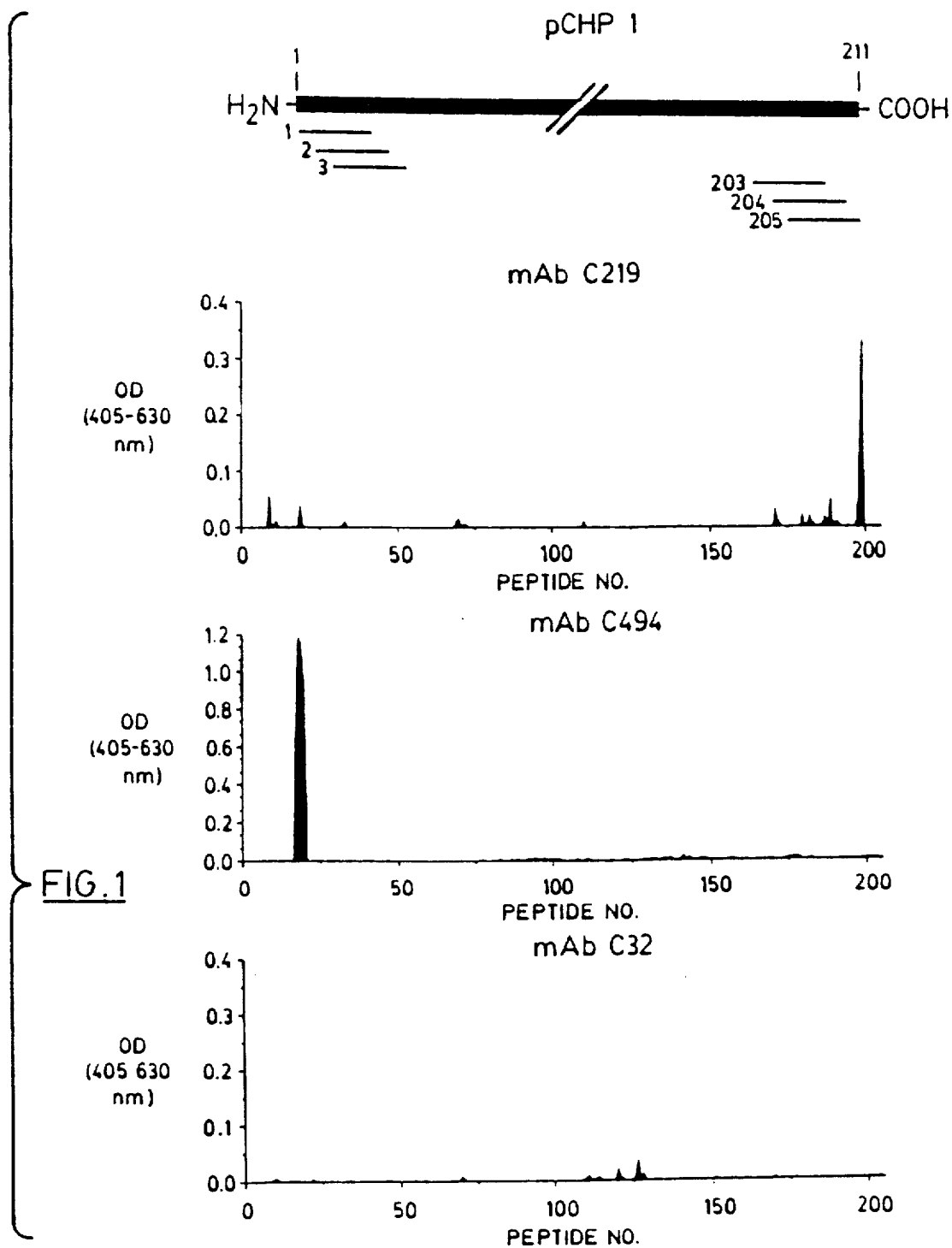
FIG. 1 provides a schematic illustration of 205 overlapping hexapeptides derived from the 211 amino acid residue polypeptide for P-glycoprotein as encoded by the clone pCHP1. Also shown are three graphs representing the optical density (absorbance) for the various hexapeptides in the presence of three different monoclonal antibodies to P-glycoprotein (C219, C494 and C32) developed by ELISA.

The development of multidrug resistant tumour cells during malignant progression is thought to be a major factor contributing to non-response in chemotherapeutic treatment of cancer. The increased expression of the membrane P-glycoprotein (relative molecular mass, Mr, 170,000) is the most consistent change observed in multidrug resistant cells in vitro, and it has been demonstrated by gene transfer studies to be causative of multidrug resistance (MDR). P-glycoprotein (Pgp) is made up of a tandem repeat containing twelve potential transmembrane domains and two putative cytoplasmic ATP binding sites (see FIG. 2). The role of P-glycoprotein as an energy dependent efflux pump was proposed from its primary sequence and structural similarity to many membrane-associated transport proteins, most notably the bacterial transport protein, hemolysin B (Gerlach, J. H. et al., Nature 324, 485–489 (1986), Gros, P. et al., Cell 47, 371-380 (1986)). The presence of P-glycoprotein has been demonstrated in a variety of human malignant tumuors. However, whether or not P-glycoprotein predicts non-response to chemotherapy remains a critical issue and requires more correlative studies (Ling, V. J. Nat. Cancer Inst. 81, 84-85 (1989)). P-glycoprotein is also found in certain normal tissues, including large intestine, adrenal glands, kidney, liver and brain. The expression of Pgp in different tissues had led to the speculation that it may play a role in normal detoxification and transport of lipophilic molecules.

Recent data indicate that P-glycoprotein is encoded by a family of three genes in rodents, and two in human (Ng, W. F. et al. Mol. Cell. Biol. 9, 1224-1232 (1989)). A comparison of the amino acid sequences among the different gene family members, or isoforms, indicate a similar overall structure (Endicott, J. A. et al. Mol. Cell Biol. 7, 4075-4081 (1987)). However, transfection studies using full-length cDNAs have suggested that only some of the Pgp isoforms confer a MDR phenotype on otherwise drug sensitive cells. The class I and II isoforms have been directly implicated in drug resistance, while the function of the class III isoform is not known (Ng supra).

Immunohistochemical staining of Pgp expression has the advantages of single cell localization and detection of polarized distribution. Until now, however, the monoclonal antibodies (mAbs) used could not address the question of differential gene expression. In relation to the present invention, the epitopes of three P-glycoprotein-specific monoclonal antibodies have been mapped to a resolution of a single amino acid. Monoclonal antibody C494 is gene specific, binding to a sequence present only in the class I isoform of hamster and human. The monoclonal antibody C32 recognizes a sequence that is conserved in hamster class I and II isoforms In contrast, the monoclonal antibody C219 recognizes a highly conserved amino acid sequence found in all Pgp isoforms characterized to date. In accordance with the invention, the epitope specific staining of these antibodies in immunohistochemical studies was confirmed by competition with specific peptides Using such reagents to examine Pgp expression in normal hamster tissues, it was observed that colonic epithelial cells express predominantly the class I isoform in a polarized manner, adrenal cortical cells express predominantly the class II isoform, while only a small percentage of skeletal muscle fibers express P-glycoprotein, the class III isoform. The occurrence of this isoform in muscle is unexpected, and suggests the presence of a specialized subset of muscle fibers which have not been identified previously.

Epitope Mapping

The epitope sequences of the three monoclonal antibodies C219, C32, and C494, were determined using a synthetic strategy devised by Geysen and his coworkers (Proc. Natl. Acad. Sci. USA 81, 3998-4002 (1984)). Overlapping hexapeptides covering the entire 211 amino acid fragment from the C-terminal cytoplasmic domain (shown previously to contain all three mAbs binding sites (Riordan, J. R. et al. Nature 316, 817-819 (1985))) Were synthesized on polypropylene pins (see Materials and Methods). Each successive pin contained the last five residues of the preceding one and the following amino acid in the sequence (FIG. 1). A library of about 250 peptides was screened by ELISA with each monoclonal antibody to determine its binding sequence C219 mAb reacted with two peptides (198 and 199), and only these peptides yielded a strong signal out of the peptides tested. The monoclonal antibody C494 reacted with four successive peptides giving a stronger signal than C219 mAb. In contrast, C32 mAb binding to synthetic hexapeptides occurred over two peaks. Although the binding of the antibody C32 to peptides 119, 120 and 125-129 resulted in weaker signals than that seen for the other two antibodies, it was nevertheless reproducible, and significantly above the background.

Figure 2:
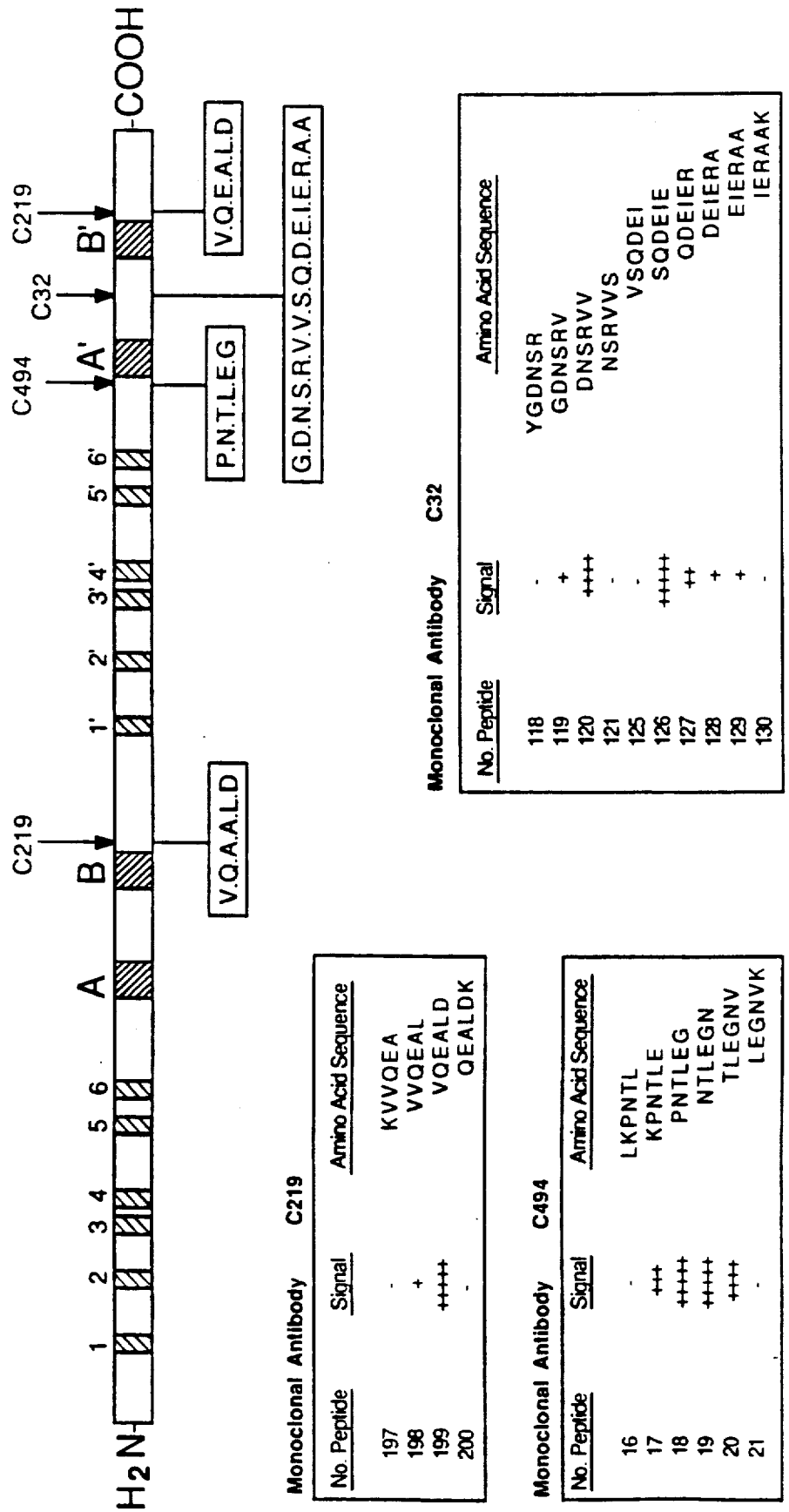
FIG. 2 shows schematically the epitope location of the three monoclonal antibodies C219, C494 and C32 on P-glycoprotein (hamster pgp2). Also shown are twelve putative transmembrane domains numbers 1-6 and 1'-6'. The two proposed A and B ATP-binding domains are indicated by the shadowed squares. The sites and the amino acid sequences (epitopes) recognized by the three monoclonal antibodies are indicated by arrows. The peptide number corresponds to the hexapeptides of FIG. 1. The absorbance signals from the ELISA are indicated as a relative value with 5 pluses representing the highest absorbance with a particular antibody.

The results tabulated in FIG. 2 represent the relative intensity of the ELISA signal obtained for the binding of the three monoclonal antibodies to the generated synthetic peptides. The movement of the six amino acid window defines the boundaries of the continuous epitopes, and identifies some of the amino acids that are critical for binding. For example, the antibody C219 bound strongly to the amino acid sequence (in single letter code) VQEALD with $val^{506}$ and $asp^{511}$ representing two critical amino acids required for antigen recognition. C494 mAb bound to four hexapeptides covering the amino acid sequence KPNTLEGNV with $thr^{323}$ and $glu^{325}$ as the critical residues. Differences in the number of hexapeptides involved in antibody binding using this assay are likely related to the size of the epitope recognized by a given antibody, and the number of residues (distance) between the critical amino acids in a given epitope. The C32 mAb binding domain covers a stretch of thirteen amino acids (GDNSRVVSQDEIER), with four critical amino acids associated with its binding, $asp^{427}$ and $val^{431}$ from the first domain, and $glu^{436}$ and $glu^{438}$ from the second. The weak signals seen for C32 mAb in FIG. 1 was due to the small size of the synthetic hexapeptides used to probe for its epitope. A comparable ELISA signal to that seen with C494 mAb was obtained with C32 mAb when the complete sequence of thirteen amino acids (GDNSRVVSQDEIER) was synthesized on a pin (results not shown). A similar extension of the peptide sequences for C219 and C494 epitopes, however, did not result in an increased signal.

IDENTIFICATION OF MONOCLONAL ANTIBODIES AS GENE SPECIFIC PROBES

The amino acid sequences of the antigenic peptides from FIG. 1 were located on the full structure of P-glycoprotein as shown in FIG. 2. The antibody C219 binds to an amino acid sequence six residues away from the consensus sequence of the B site of the proposed ATP binding domain. A homologous amino acid sequence for C219 mAb is also found in the N-terminal half of Pgp. The epitope recognized by C494 mAb is on the other side of the ATP binding domain to that of C219. C32 monoclonal antibody binds to a region positioned between the A and B sites of the postulated ATP binding domain. However, the N-terminal half of Pgp does not contain a homologous sequence for the C494 or C32 epitope.

FIG. 3 shows a comparison of the antibodies binding regions among the different members of the Pgp gene family characterized to date from hamster, human, and mouse. The C219 binding site is conserved in both the C- and N-terminal halves of all Pgp isoforms. The finding that C219 epitope sequences are conserved in all mammalian P-glycoproteins points to the usefulness of this antibody as an immunological probe to quantitate the levels of P-glycoprotein in cell lines and tumour tissues. Moreover, since the epitope for C219 is found in both halves of the P-glycoprotein molecule, in different gene members, and in different species, it must have been conserved through evolutionary history. It is interesting that the bacterial transport protein hemolysin B which is structurally very similar to P-glycoprotein, especially in the ATP binding domain, does not contain this particular epitope. Thus, this epitope sequence in P-glycoprotein may represent a functional difference between these highly homologous proteins.

The C494 epitope is found only in the human (mdr1) and hamster (pgp1) class I gene product. The monoclonal antibody C494 does not recognize the other Pgp isoforms since their analogous sequences contain a substitution of a critical amino acid (thr$^{323}$). This finding demonstrates the specificity of the antibody C494, and argues for its use as a class I gene specific probe. In vitro transfection studies have demonstrated that human class I gene (mdr1) can confer MDR in a variety of cells. Thus, positive staining with the C494 antibody may be diagnostic of cells expressing the MDR phenotype in human tissues.

A comparison of sequences analogous to the C32 mAb binding site from the different members of the Pgp gene family reveals that the hamster class I and II molecules have the requisite amino acid sequence for this monoclonal antibody. This sequence differs from those of the other P-glycoproteins characterized to date at a critical amino acid (glu$^{438}$ to val$^{438}$). Therefore, this antibody is expected to bind very strongly to hamster class I and II isoforms, but only weakly to hamster class III isoform and the Pgp isoforms of human and mouse.

FIG. 4 lists the relative signals from the ELISA tests performed using analogous peptide sequences from the different Pgp isoforms. The binding of C219 mAb to the peptide sequence VQAALD in the N-terminal half was stronger than that seen for the epitope sequence VQEALD in the C-terminal half, due to a single amino acid substitution (ala substituted for glu$^{508}$). The substitution of val for glu$^{508}$ in the N-terminal half of human class I Pgp isoform (VQVALD) reduced its binding to the antibody (FIG. 4). The ability to immunoprecipitate a protein fragment containing the N-terminal ATP binding domain from an in vitro expression system with C219 antibody (Endicott, Georges, and Ling unpublished observation) further corroborate the results seen using the synthetic peptides.

The specificity of the monoclonal antibody C219 was investigated further using a series of synthetic hexapeptide analogues starting with the C219 epitope sequence and replacing in turn each residue by one of the other 19 genetically coded amino acids (results will be detailed elsewhere). For example, it appears that the third position in the C219 epitope sequence (VQEALD) can tolerate a number of substitutions such as val, ala, or asp without a great loss in binding. However replacement with other amino acids such as his, gly, lys, or pro resulted in minimal or no binding to the antibody. A search through the Genbank database for amino acid sequences similar to that of C219 epitope sequence (VQEALD) revealed an amino acid sequence VQHELD in myosin heavy chains (rat cardiac muscle), and the sequence VQEALE in DNA polymerase (Bacteriophage T4). These sequences are not recognized by the antibody C219 since such amino acid substitutions did not produce peptides that bound to the antibody. Myosin heavy chain protein used in the molecular weight standards (Amersham) mix did not stain with C219 mAb by Western blot analysis.

The results from the ELISA for the binding of peptide analogues of the C494 epitope indicated that a substitution of a single critical amino acid (thr$^{323}$) to trp in class II hamster (pgp2), or lys in class III hamster (pgp3) and human (mdr3) results in complete loss of antibody recognition. These results confirm that the monoclonal antibody C494 is a specific immunological probe for the expression of human (mdr1) and hamster (pgp1) P-glycoprotein class I isoform (FIG. 4). Analogues for only part of the C32 mAb binding domain (SQDEIER) were synthesized since the remainder of the same antibody binding domain is conserved among the different members of Pgp gene family (FIG. 3). The values tabulated in FIG. 4 demonstrate the effect of a single critical amino acid substitution on the binding of C32 mAb to this peptide (e.g. val substituted for glu$^{438}$ fail to bind the antibody). Therefore, the monoclonal antibody C32 should bind most strongly to hamster class I and II products, and much more weakly to the other Pgp isoforms. In agreement with the above conclusion, previous results have demonstrated that hamster P-glycoprotein binds more strongly to C32 mAb than that of mouse and human using a Western blot technique.

IMMUNOHISTOCHEMICAL STAINING

An immunohistochemical study of normal hamster tissues was undertaken, in which serial sections of each tissue were incubated with each of the three mAbs, either in the absence or in the presence of the peptide containing the respective epitope sequence. Specific staining by monoclonal antibody against Pgp was defined as staining that could be completely abolished by competition with a 100-fold molar excess of the peptide containing the antibody epitope. This method allows for the positive identification of epitope specific staining, and is in contrast to conventional immunohistochemical staining whereby an "irrelevant" antibody is used as a negative control.

Uncompetable staining with all three antibodies was frequently observed. Notably, this included strong membrane staining of epithelial cells of seminal vesicles, distinct staining of cells of colonic crypts, and moderate intracytoplasmic staining of hepatocytes. Such staining is likely due to non-specific interactions with the antibody through regions other than those containing the paratope domain. Thus, the use of peptides in a competitive binding assay can clearly result in enhanced specificity and sensitivity of the immunohistochemical procedure.

Figure 5A:
FIGS. 5a-f show epitope specific staining of P-glycoprotein isoforms in relation to normal hamster tissues.
Figure 5B:
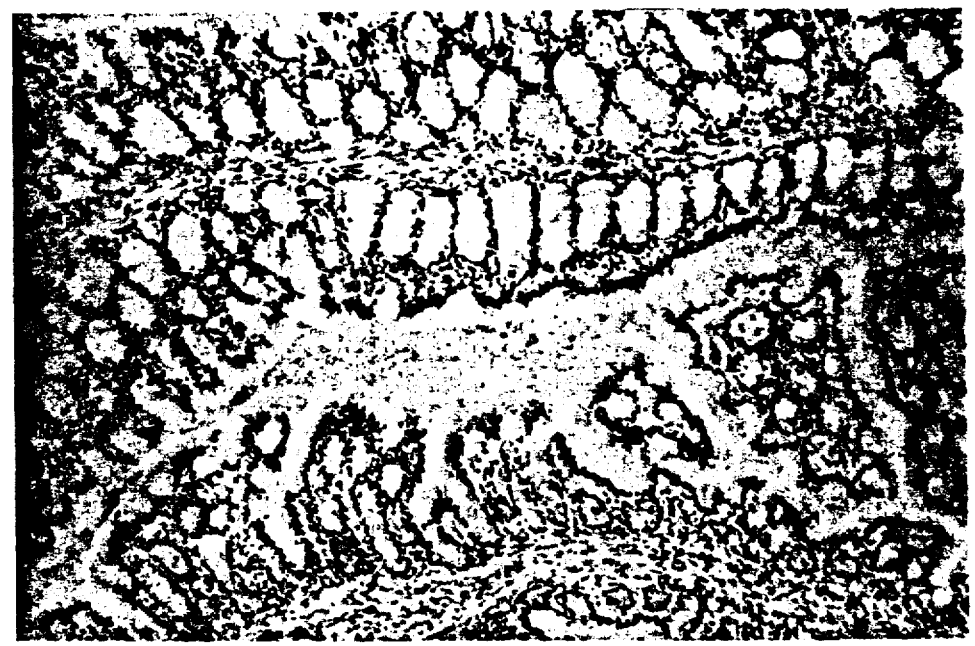

The epitope mapping studies predict that three distinct patterns of reactivity with the mAb panel would result from the expression of each of the three hamster Pgp isoforms (Table I). The staining of intestinal tissue sections with C494 mAb alone (FIG. 5a), and in the presence of a peptide containing the C494 mAb epitope (FIG. 5b) revealed a strong signal for the luminal surface of colonic epithelial cells which is abolished when the free peptide was added. A similar staining is observed with C219 and C32 mAbs (results not shown). This staining pattern is consistent with the predominant expression of Pgp1 isoform (see Table I). The immunohistochemical staining shows that the class I isoform has a polarized distribution in the colonic epithelial cell membrane. This pattern of pgp isoform expression are consistent with a membrane transport function, possibly for the active extrusion of toxic molecules.

TABLE I

| Epitope Distribution of Pgp Isoforms | | | |
|---|---|---|---|
| P-glycoprotein isoforms | Epitopes | | |
| Classes | C219 mAb | C32 mAb | C494 mAb |
| I (Hamster pgp1) | + | + | + |
| II (Hamster pgp2) | + | + | − |
| III (Hamster pgp3) | + | − | − |
| I (Human mdr1) | + | − | + |
| III (Human mdr3) | + | − | − |
| II (Mouse mdr1) | + | − | − |
| III (Mouse mdr2) | + | − | − |

Figure 5C:
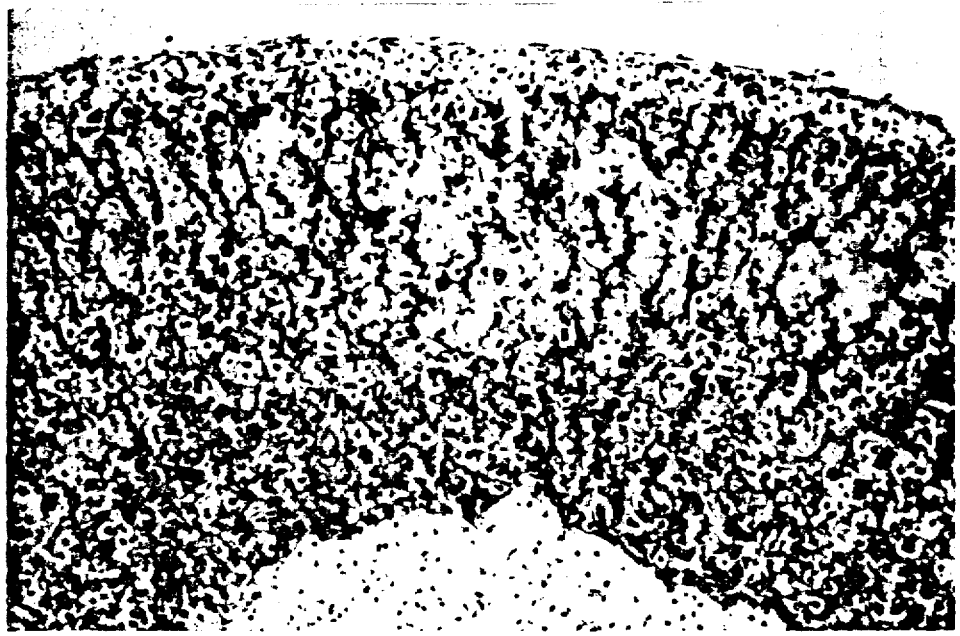
Figure 5D:

FIGS. 5c and 5d show the staining of adrenal tissue sections with C32 mAb in the absence, and presence of its epitope, respectively. The plasma membrane of adrenal cortical cells is stained with C32 and C219 mAbs only, indicating the predominant expression of the class II Pgp isoform (see Table I). Previous reports of P-glycoprotein expression in the adrenal gland have raised the possibility that Pgp may be involved in the transport of corticosteroids. In this study the detection of Pgp in the steroid producing zona fasciculata and zona reticularis, agree with the above hypothesis. However, cortical cells in the zona glomerulosa, also known to produce steroids, do not express detectable levels of P-glycoprotein and this suggests that Pgp is not a general mechanism for secreting steroids, but that it may be a marker of differentiation of specialized cortical cells. Since the immunohistochemical technique described here is semiquantitative, it was not possible to determine if tissues exhibiting the class I pattern of staining also expressed much lower levels of the other two isoforms. Similarly, tissues exhibiting the class II staining pattern may also express the class III isoform at low levels.

Figure 5E:
Figure 5F:
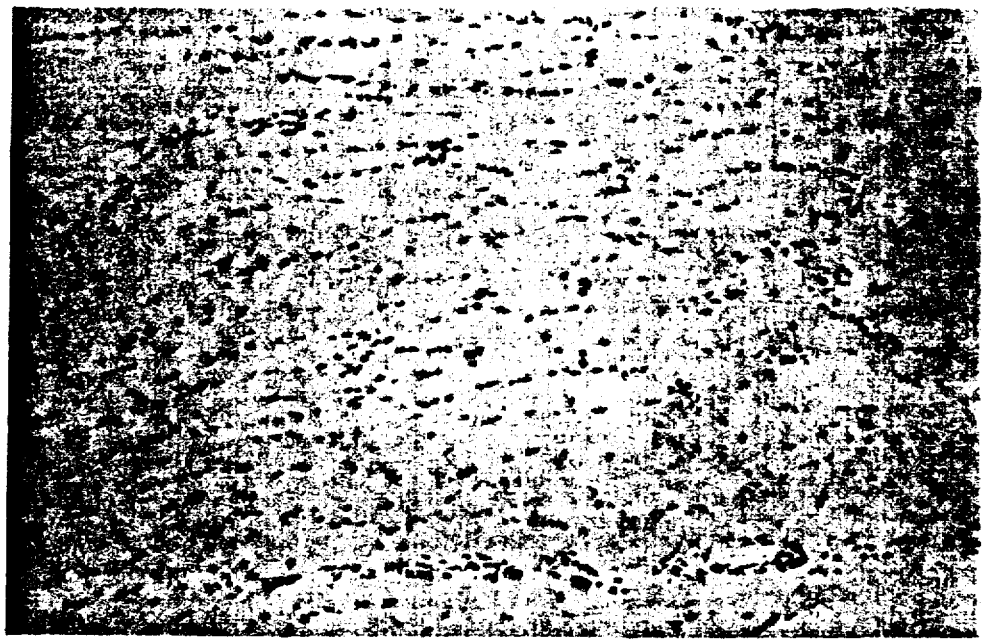

Serial sections of hamster skeletal muscles incubated with C219 mAb (FIG. 5e) stained approximately 5% of muscle fibers. The staining signal of these fibers was completely abolished in the presence of the peptide containing C219 mAb epitope (FIG. 5f). Staining of skeletal muscle with C32 or C494 did not reveal epitope specific staining. This staining pattern is specific to a class III isoform expression alone (Table I). The expression of the class III isoform was previously observed in Northern blot analysis (mdr2 positive) of mouse muscle tissue, and Western blot analysis (C219 positive and C494 negative) of human muscle tissue. However, it could not be determined in those studies that the expression of the class III isoform was localized to a subset of muscle fibers as shown here. Skeletal muscle from a variety of locations (chest wall, paraspinal, diaphragm, thigh, and anterior abdominal wall) show two distinct types of fibers, with the majority of fibers lacking detectable amounts of Pgp while less than 10% of fibers express high levels of the class III isoform. The distribution of this isoform within muscle fibers follows a fairly regular, coarse, transverse pattern, in addition to patchy areas of plasma membrane staining. Ultrastructural studies are ultimately required to localize Pgp to subcellular structures in skeletal muscle fibers, but it is likely a membrane component, for example, a component of T-tubules. The finding that the class III isoform is expressed only in a subset of muscle fibers is unexpected. It could be speculated that muscle fibers expressing the class III Pgp isoform perform specialized function not previously recognized. For example, it may be involved in the energy-dependent transport of metabolites across the complex membrane system of some skeletal muscle fibers.

DISCUSSION

Competition experiments with hexapeptides precisely mapped the epitopes of the three different monoclonal antibodies against P-glycoprotein. The monoclonal antibodies were shown to bind to "continuous" epitopes consisting of critical amino acids located within a few residues from each other. The fact that all these epitopes are of this type may be due to the original screening (SDS-denatured proteins in a dot blot assay) for these antibodies. However, all these mAbs can bind to the native form of the P-glycoprotein. It is likely that this mapping technique will be applicable for defining epitopes of other mAbs generated in this manner.

The expression of P-glycoprotein in normal tissues and cell lines has been analyzed using various biochemical techniques. Immunohistochemical staining of tissues has the advantages of detecting polarized expression, as well as, the simultaneous visualization of P-glycoprotein in tissue sections containing both normal and tumour cells. However, as in any immunohistochemical detection assay, a high level of staining specificity is sometimes compromised in an effort to increase sensitivity. In this study a high level of staining specificity and sensitivity has been achieved through the combined use of monoclonal antibodies with epitope-specific peptides in a competitive immunohistochemical assay. For example, as pointed out earlier, non-competable staining was frequently observed in many tissues, and this was assumed to be due to nonspecific interaction. The staining of a subset of muscle fibers with C219 mAb in muscle tissue was unexpected and this was initially assumed to be due to crossreactivity of the mAb with myosin (Thiebaut, F. et al. J. Histo. & Cyto, 37, 159-164 (1989)). However, in the present study epitope specific peptides were used in a competitive immunohistochemical analysis which demonstrated that this staining is most likely due to the presence of the class III Pgp isoform in a subset of muscle fibers. Previous immunohistochemical studies of P-glycoprotein expression in normal tissues and tumour samples have provided insight into the cellular localization of this membrane glycoprotein, however it has not been possible to distinguish what classes of Pgp isoforms are expressed at the protein level. The results of the epitope mapping studies described here suggest that the three classes of mAbs, represented by C219, C32, and C494, may be used in combination to determine the pattern of expression of the Pgp isoforms in normal and tumour tissues. This may have applications in studies for investigating the correlation of P-glycoprotein expression with patient response to cancer chemotherapy.

MATERIALS AND METHODS

Prederivatized plastic pins and polypropylene trays were obtained from Cambridge Research Biochemicals (Valley Stream, N.Y.). Active esters of Fmoc amino acids were supplied by MilliGen (Millipore, Bedford, Mass.). Glass-distilled dimethylformamide (DMF) was purchased from Anachemia (Montreal) and kept on 4 A molecular sieves at 4° C. for 2 to 3 weeks. The amine content was monitored by the dinitrofluorobenzene assay. Only DMF giving an absorbance value at 381 nm below 0.10 as compared to a reagent blank was used in the synthesis. Reagent grade dichloromethane (DCM) and methanol (MeOH) were purchased from BDH Chemicals (Montreal) and used without further purification. Other suppliers are listed as follows: piperidine from Fisher Scientific (Toronto, Ontario), PAM resins from Applied BioSystems (Foster City, Calif.), Boc amino acids from IAF Biochemicals (Montreal, Quebec), dicyclohexylcarbodiimide (DCC) from Aldrich Chemical Co. (Milwaukee, Wisc.), sequencing-grade trifluoroacetic acid (TFA) and diisopropylethylamine (DIEA) from Chemical Dynamics Corp. (South Plainfield, N.J.).

SOLID-PHASE PEPTIDE SYNTHESIS ON PLASTIC PINS

Overlapping hexapeptides were synthesized on polyethylene pins as described earlier (Geysen, H. M. et al. supra). The peptides were assembled on the pins in the C-to-N terminus direction using 9-fluorenylmethyloxycarbonyl (Fmoc) protected amino acids. Briefly, the plastic pins were arranged on polypropylene block supports in a pattern suitable for soaking the tip of each pin into individual well of 96-well polypropylene plates. The pins were prederivatized with a non-detachable 15-atom long spacer ending with a Fmoc-b-alanine group. All steps in the synthesis were performed at room temperature. The pin blocks were initially soaked for 30 minutes in a 20% (v/v) piperidine/DMF bath to remove the Fmoc group generating a free terminal amino group. The pins were then cycled through the following steps: DMF washes (2 times; 2 minutes), methanol washes (3 times, 2 minutes), the pins were air-dried for 15 minutes, soaked in DMF (5 minutes) and blotted gently with tissue paper. The preformed active esters (oxobenzotriazine esters for serine and threonine; pentafluorophenyl esters for all other amino acids) of Fmoc amino acids (30 mM) were then dissolved in DMF containing 1-hydroxybenzotriazole (30 mM). The solutions were then dispensed immediately in the appropriate wells of 96-well polypropylene plates. The coupling step was initiated by placing the tip of the pins in their respective wells. The pin blocks and the polypropylene plates were carefully placed in sealed plastic trays and the coupling reactions were left to proceed overnight. The Fmoc deprotection and subsequent steps were then repeated until all hexapeptides were completed. The final Fmoc group on the completed peptides was removed as described above and the resulting free amino group was acetylated (DMF: acetic anhydride: diisopropylethylamine 50:5:1 (v/v/v); 90 minutes). The side-chain protecting groups of all peptides were simultaneously cleaved by soaking the pins in trifluoroacetic acid:phenol:ethanedithiol 95:2.5:2.5 (v/v/v) for 4 hours. The pins were successively washed with dichloromethane (twice for 2 minutes), neutralized with 5% DIEA/DCM (twice for 5 minutes), followed by single dichloromethane wash (5 minutes), air dried (15 minutes), wetted in water for 2 minutes, and soaked in methanol overnight. Remaining traces of solvent were evaporated under vacuum and the blocks were stored in plastic containers at room temperature in the presence of dessicant. Amino acid analysis was performed on ten pins. The peptide substitution per pin ranged in value from 2 to 4 nanomoles.

ELISA

Peptides coupled to solid support polypropylene pins were incubated in phosphate buffered saline, pH 7.4 (PBS) for 30 min. at room temperature. Pins were then soaked for 1 hour in a blocking buffer (1% w/v ovalbumin, 1% w/v bovine serum albumin (BSA), 0.1% v/v Tween 20 in PBS) to reduce non-specific adsorption of antibodies. Alternatively, the wells of a 96-well ELISA plates were coated with solutions of the free peptides dissolved in PBS. The plates were incubated overnight at room temperature and washed once with PBS. All unreacted sites were blocked with 3% BSA solution. The pins were incubated overnight at 4° C. in wells containing 100 μl aliquots of primary antibody solutions (0.5-2.0 μg/ml dissolved in coating buffer). After one hour incubation with peroxidase conjugated goat anti-mouse antibody, pins were washed four times with PBS solution containing 0.05% (v/v) Tween 20. The binding of antibody to peptides was detected by incubating the pins for 30 minutes with a freshly prepared solution of azino-di-3-ethylbenzthiazdinsulphonate (ABTS) in 1M citric acid pH 4.0. Measurements of color development were made at 405-630 nm using the microplate reader (EL30 Bio-Tek instrument). Antibodies bound to the pins were stripped off the solid-supports by sonicating the pins for 30 minutes at 65° C. in 0.1M sodium phosphate solution containing 1% sodium dodecyl sulfate (SDS) and 0.1% (v/v) 2-mercaptoethanol. The pins were rinsed in warm distilled water (50°-60° C.) and finally washed in a bath of boiling methanol.

IMMUNOHISTOCHEMICAL STAINING

Normal adult Chinese hamsters were sacrificed in a carbon dioxide chamber. Organs and tissues were removed at 4° C. within 1 hour of sacrifice, and frozen in isopentane chilled with dry ice. Frozen sections (8 μm) were cut and fixed in cold acetone (10 minutes at 4° C.), then stained for Pgp using an avidin-biotin-peroxidase complex technique. The primary antibody (C219, C32, or C494) was used at 10 μg/ml in 1% BSA/PBS. One hour prior to incubation of tissue sections with the primary antibody, the antibody solution was pre-incubated with 100-fold molar excess of either the peptide encoding the antibody epitope or an irrelevant peptide. This sufficiency of excess peptide was based on a competitive binding assay in which Pgp immobilized on nitrocellulose filter was allowed to react with each mAb in the presence of increasing concentrations of either the peptide encoding the mAb epitope or an irrelevant peptide. Competitive binding of the primary antibody to the peptide and to Pgp present in tissues proceeded for 1 hour at room temperature in a humidified chamber. The sections were washed with PBS and incubated sequentially with biotinylated horse-antimouse antibody and with avidin-biotin-peroxidase complex (Vector Laboratories, Burlingame, Calif.) according to manufacturer's instructions. The binding of the antibody to tissues was detected by 5 minutes' incubation with 3,3'-diaminobenzidine tetrahydrochloride (1 mg/ml; Sigma) and hydrogen peroxide (0.003%). Tissues were counterstained with hematoxylin, dehydrated and mounted in Permount.

We claim:

1. An immunoassay method for determining the specificity of binding of a monoclonal antibody to an antigen, wherein the epitope for the antibody has been mapped to the level of a single amino acid to determine the critical amino acids for binding of the antibody and the correct sequence for such amino acids, comprising:
    contacting a first portion of a test substance with the monoclonal antibody, incubating the resulting mixture to promote binding of the antibody to available antigen associated with the test substance, and testing for binding of antibody to the test substance;

if binding of antibody to the first portion of test substance is demonstrated, contacting a second portion of the test substance with the monoclonal antibody which has been pre-incubated with at least an excess amount of a peptide encoding the mapped antibody epitope for the antigen having the critical amino acids for binding of the antibody in the correct sequence, said excess amount being sufficient to ensure occupation of substantially all antibody binding sites for the epitope, incubating the resulting mixture to promote binding of the antibody to any available antigen associated with the test substance, and testing for binding of antibody to the test substance; and comparing the results for the binding of the antibody to the first and second portions of the test substance to determine the specificity of antibody binding.

2. An immunoassay method as claimed in claim 1, wherein the immunoassay is ELISA, RIA or immunohistochemical staining.

3. An immunoassay method as claimed in claim 1, wherein the monoclonal antibody is specific against P-glycoprotein.

4. An immunoassay method as claimed in claim 3, wherein the monoclonal antibody is C219, C494 or C32.

5. An immunoassay method as claimed in claim 3, wherein the immunoassay is immunohistochemical staining.

6. An immunoassay method as claimed in claim 3, wherein the monoclonal antibody is C219 and the peptide encoding the antibody epitope consists essentially of the sequence VQEALD.

7. An immunoassay method as claimed in claim 3, wherein the monoclonal antibody is C494 and the peptide encoding the antibody epitope consists essentially of the sequence NTLEG.

8. An immunoassay method as claimed in claim 3, wherein the monoclonal antibody is C32 and the peptide encoding the antibody epitope consists essentially of the sequence GDNSRVVSQDEIE.

* * * * *